(12) United States Patent
Smolyaninov et al.

(10) Patent No.: US 6,897,436 B2
(45) Date of Patent: May 24, 2005

(54) SYSTEM AND METHOD FOR OPTICAL PROCESSING BASED ON LIGHT-CONTROLLED PHOTON TUNNELING

(75) Inventors: Igor I. Smolyaninov, Columbia, MD (US); Christopher C. Davis, Bowie, MD (US); Anatoly Zayats, Belfast (GB)

(73) Assignee: University of Maryland, Riverdale, MD (US)

(*) Notice: Subject to any disclaimer, the term of this patent is extended or adjusted under 35 U.S.C. 154(b) by 143 days.

(21) Appl. No.: 10/455,339

(22) Filed: Jun. 6, 2003

(65) Prior Publication Data
US 2003/0227662 A1 Dec. 11, 2003

Related U.S. Application Data
(60) Provisional application No. 60/386,508, filed on Jun. 6, 2002.

(51) Int. Cl.[7] ............... H01J 3/14; H01S 3/00
(52) U.S. Cl. ............... 250/234; 359/244
(58) Field of Search ............... 372/7; 359/244, 359/237; 250/234, 306–309, 73

(56) References Cited

U.S. PATENT DOCUMENTS

| | | | |
|---|---|---|---|
| 5,018,865 A | * | 5/1991 | Ferrell et al. ............... 356/600 |
| 5,349,443 A | * | 9/1994 | Guerra ............... 356/600 |
| 5,754,514 A | * | 5/1998 | Guerra ............... 369/116 |
| 5,774,221 A | * | 6/1998 | Guerra ............... 356/602 |
| 5,939,709 A | * | 8/1999 | Ghislain et al. ............... 250/216 |

* cited by examiner

Primary Examiner—Wilson Lee
Assistant Examiner—Hung Tran Vy
(74) Attorney, Agent, or Firm—Rosenberg, Klein & Lee

(57) ABSTRACT

A system (10) for optical processing based on light-controlled photon tunneling is provided. The system (10) includes a prism (12) having a metallic film layer (14) formed on an upper surface thereof. The metallic film layer (14) has a microscopic aperture (18) formed therethrough and the microscopic aperture (18) is covered by a layer of non-linear optical film. A first light beam (30) is projected towards aperture (18) and photons from first light beam (30) tunnel through aperture (18). A second light beam (32) is also projected towards microscopic aperture (18), with the second light beam (32) having a different wavelength than that of light beam (30). Selective actuation and modulation of light beam (32) allows for selective control over the rate and intensity of the photons which tunnel through microscopic aperture (18). The intensity of transmission of the photons from light beam (30) are measured by optical fiber tip (22), thus allowing for the creation of optical gates, switches, and other optical processing devices.

22 Claims, 4 Drawing Sheets

SYSTEM AND METHOD FOR OPTICAL PROCESSING BASED ON LIGHT-CONTROLLED PHOTON TUNNELING

This application claims benefit of provisional application 60/386,508 filed Jun. 6, 2002.

BACKGROUND OF THE INVENTION

1. Field of the Invention

The subject invention relates to a system and method for optical processing based on light-controlled photon tunneling. In general the subject system and method utilizes the properties of single-photon tunneling through a microscopic aperture for the creation of optical switching, gating, and processing devices. The photons generated by a first light source tunnel through the microscopic aperture which is covered with a non-linear film layer. A second light source generates a second light beam which is directed towards the aperture and modulation of the second light beam allows for selective and controlled modulation of the tunneling of the photons generated by the first light source.

In a particular example, the present invention directs itself to an optically refractive medium which may be a prism having a metallic layer deposited on an upper surface thereof with at least one microscopic aperture being formed through the metallic layer. More particularly, a non-linear optical film layer is formed on the metallic film layer covering the microscopic aperture. A first light source generates a first light beam which is transmitted to the microscopic aperture, the photons of which tunnel through the microscopic aperture.

Further, a second light source generates a second light beam having a differing wavelength from that of the first light beam, and the second light beam is also directed at the microscopic aperture formed through the metallic film layer. Selective actuation of the second light source prevents the tunneling of the photons of the first light beam through the metallic film layer and the non-linear optical film layer, thus allowing for the selective control, or switching, of the photon tunneling.

Further, an optical fiber tip is positioned above the microscopic aperture and contacts the non-linear optical film layer. The optical fiber tip, in conjunction with a control mechanism for controlling position and movement of the tip, allows for measurement of the intensity of light which has tunneled through the metallic film layer and the non-linear optical film layer. The system for optical processing based on light-controlled photon tunneling of the present invention may be used for the creation of optical gates, switches, or other optical processing devices.

2. Prior Art

The theory of photon tunneling through non-linear optical media is known in the prior art. However, to Applicants' knowledge, no physical devices utilizing photon tunneling for the purposes of optical switching or gating are to be found in the prior art. It is not believed that the prior art provides for the concept of generating at least first and second light sources of differing wavelengths being directed to microscopic apertures or nanoholes for controlling the tunneling of photons to obtain the purposes and objectives of the instant invention concept. Additionally, single-electron tunneling devices are known in the art, however, the present invention directs itself to a system and method for utilizing single-photon tunneling for producing optical gates, optical switches, and other optical processing devices.

SUMMARY OF THE INVENTION

The present invention provides for a system and method for optical processing based on light-controlled photon tunneling. The system uses a prism having a metallic film layer deposited thereon, with the metallic film layer having at least one microscopic aperture formed therethrough. A non-linear optical film layer is formed on the metallic film layer and covers the microscopic aperture. A first light source generates a first light beam which is transmitted to the microscopic aperture. Photons of the first light beam, having a first wavelength, tunnel through the microscopic aperture. A second light source generates a second light beam having a second wavelength with the second light beam also being transmitted to the microscopic aperture. The second light beam, however, prevents the tunneling of the photons of the first light beam through the metallic film layer and the non-linear optical film layer. Thus, selective actuation of the second light source allows for the selective switching or gating of the photon tunneling, which provides for an optical switching, gating, or other processing device.

It is a principal objective of the subject system and method for optical processing based on light-controlled photon tunneling to provide a metallic film layer having a microscopic aperture formed therethrough and formed on an upper surface of a prism.

It is a further objective of the subject invention to provide a non-linear optical film layer formed on the metallic film layer with the non-linear optical film layer covering the microscopic aperture.

It is a further objective of the subject invention concept to provide first and second light sources for generating first and second light beams, each having a unique wavelength, and directing the first and second light beams at the microscopic aperture formed through the metallic film layer.

It is an important objective of the present invention to provide selective actuation of the second light source, thus allowing for selective tunneling of photons from the first light beam through the metallic film layer and the non-linear optical film layer.

It is a further important objective of the present invention concept to provide an optical fiber tip positioned above the microscopic aperture and in contact with the non-linear optical film layer for measuring the intensity of photons tunneling through the metallic film layer and the non-linear optical film layer.

DESCRIPTION OF THE PREFERRED EMBODIMENTS

Figure 1:
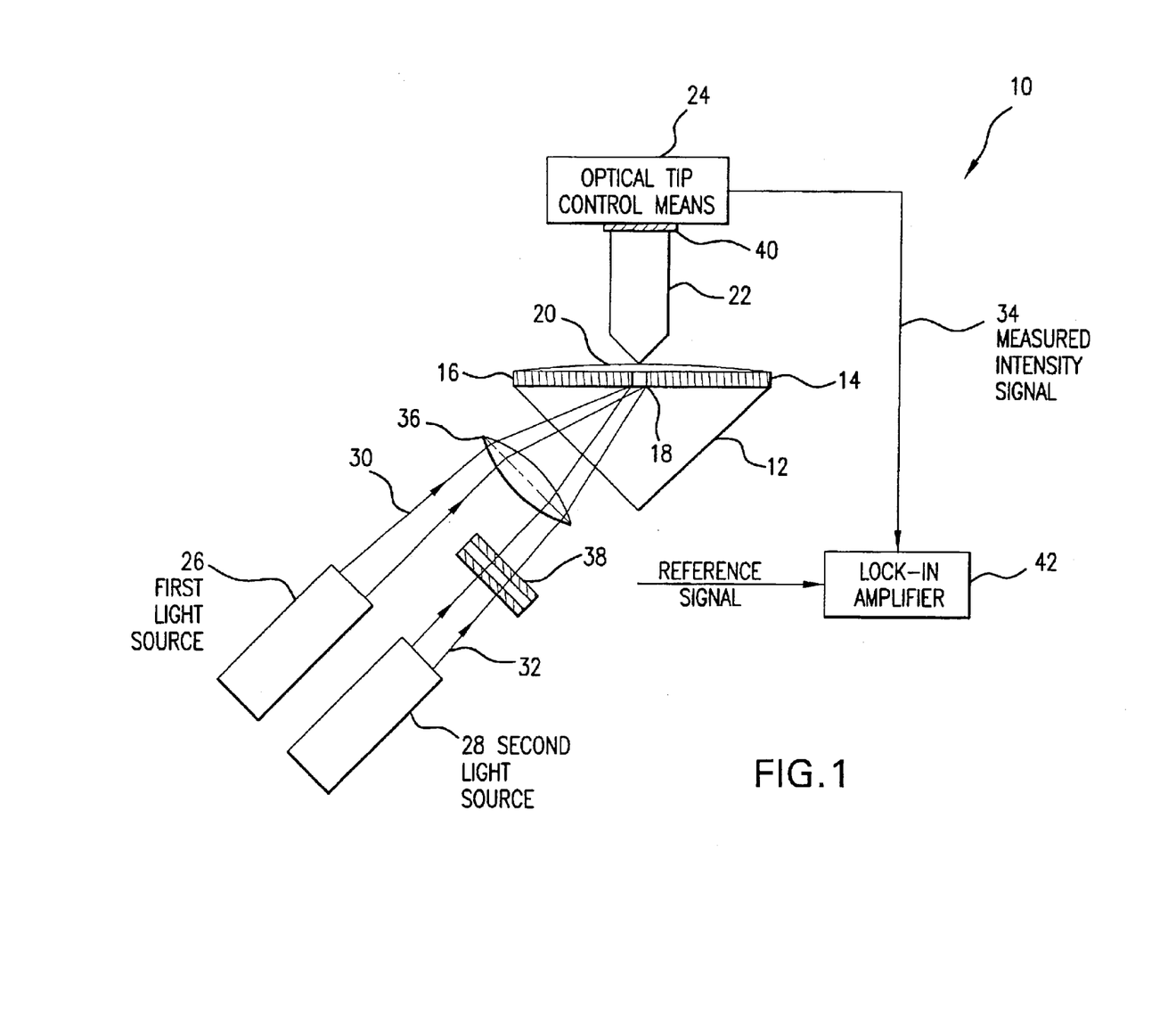
FIG. 1 is a schematic diagram illustrating the system for optical processing based on light-controlled photon tunneling.

Referring to FIG. 1, there is shown a system 10 for optical processing based on light-controlled photon tunneling. The system 10 acts as a gate or switch for controlling the tunneling of photons from a first light beam 30 through a microscopic aperture or pin hole 18 formed in a film layer 14. This optical gate or switch may be used in optical processing systems and opto-electronic devices.

System 10 utilizes photon tunneling as the basis of the formation of an optical processing system. Photon tunneling is analogous to electron tunneling, which is widely used in opto-electronic systems, such as scanning tunneling microscopes, which are well-known in the art. In scanning tunneling microscopes, for example, the tunneling current is proportional to the local density of states (LDOS) of a sample under investigation at the Fermi energy. Single-electron tunneling can be realized in systems in which tunneling electrons significantly modify the energy spectrum of the LDOS by, for example, influencing the Fermi energy of the sample.

The LDOS for photons (sometimes referred to as the photonic mode density) can be defined in the same way as done for electrons via the electric field dyadic Green function $G(r,r'\ \omega)$ of a system under consideration:

$$\rho=(r,\hbar\omega)=-1/\pi Im G(r,r',\hbar\omega), \tag{1}$$

where $\rho$ represents the local density of states and where $\omega$ represents frequency. Equation (1) gives the density of states of electromagnetic eigenmodes of energy $\hbar\omega$. The physical interpretation of the LDOS in optics is that it is directly related to the square of the modulus of the electric field at a given point in space "r" and at a given photon energy $\hbar\omega$, and, therefore, to the electromagnetic field enhancement in the system.

Similar to single-electron tunneling, which is observed in systems in which tunneling electrons significantly modify the energy spectrum of LDOS, tunneling photons can significantly modify the LDOS spectrum of the system exhibiting third-order nonlinear effects through local changes of the dielectric constant. As a consequence of the refractive index change, the polarizability and, therefore, the LDOS of the system are modified.

A nonabsorbing electro-optical nonlinearity is employed to avoid optical losses in a nonlinear material. For a particle made of dielectric material with a low dispersion refractive index, the LDOS has a broad continuous spectrum, thus requiring significant intensities of the incoming light for controlling the particle polarizability. In contrast, small metallic particles made of gold or silver exhibit a narrow-band LDOS spectrum in the spectral range where localized surface plasmons are excited. In the maximum of the band, a significant enhancement of the electromagnetic field occurs in the vicinity of the particle, which in turn enhances the nonlinear effects. Thus, realization of light controlled photon tunneling is achieved by combining high third-order nonlinear materials with good metals exhibiting a narrow spectrum of the LDOS and strong field enhancement effects.

As shown in FIG. 1 of the Drawings, the system 10 includes a prism 12 having an upper surface 14. The prism 12 may be fabricated of glass or any other suitably optically transparent and transmissive material. In the context of this invention concept, the term prism relates to any optically transparent refractive medium. Formed on the upper surface 14 of prism 12 is a metallic film layer 16. Although the metallic film layer 16 may be formed from any one of a number of suitable metallic materials, in the preferred embodiment, metallic film layer 16 is formed from gold and has a thickness of approximately 0.5 micrometers.

Gold is chosen for the composition of the metallic film layer 16 in the preferred embodiment due to its chemical stability under ambient conditions. Gold does not typically oxidize and, thus, allows the sample to remain stable over extended periods of time.

The metallic film layer 16 has at least one microscopic aperture or pin hole 18 formed therethrough. Although FIG. 1 illustrates only one aperture or pin hole 18, this is only for illustrative purposes and the metallic film layer 16 may have a plurality of pin holes or apertures 18 formed therethrough. The pin holes or apertures 18 preferably have a very low optical transmission of a few hundred photons per second. The width "a" of each microscopic pin hole 18 may be estimated as a few nanometers using the Bethe-Boukamp expression, $$S \sim \alpha^2(\alpha/\lambda)^4, \tag{2}$$

for the cross-section of a sub-wavelength aperture, where S represents the cross-section and $\lambda$ is the wavelength of the transmitted light.

Formed on the metallic film layer 16 is a non-linear optical film layer 20. The material for the non-linear film layer 20 has a large fast nonresonant optical non-linearity. In the preferred embodiment, the non-linear optical film layer 20 is formed of poly-3-butoxy-carbonyl-methyl-urethane (3BCMU) polydiacetylene. Other suitable materials, such as poly-4-butoxy-carbonyl-methyl-urethane (4BCMU) polydiacetylene may be used, as well as other polydiacetylene materials and other non-resonant optical non-linear materials.

Referring once again to FIG. 1, an optical fiber tip 22 is positioned above or adjacent the microscopic aperture or pin hole 18 and is in contact with the non-linear optical film layer 20. The optical fiber tip 22 may be a bent optical fiber tip similar to the bent tips often used in near-field optical microscopes which are well-known in the art. The optical fiber tip 22 is used to collect light transmitted through microscopic aperture 18. Tip 22 is sensitive enough to detect single-photon tunneling through aperture 18.

The optical fiber tip 22 is coupled to a control mechanism 24. Control mechanism 24 controls the positioning and movement of the optical fiber tip 22. Control mechanism 24 may be a far-field optical microscope or a shear-force distance control system, as commonly used in near-field optical devices. Both far-field optical microscopes and shear-force distance control systems are well-known in the art.

As further shown in FIG. 1, a first light source 26 generates a first light beam 30. First light source 26 is preferably a laser, however, may be any suitable means for producing electromagnetic radiation. Similarly, a second light source 28 is provided and second light source 28 is, preferably, a laser, however, may be any suitable source of electromagnetic radiation. As shown in FIG. 1, second light source 28 produces a second light beam 32 and both first light beam 30 and second light beam 32 are directed to microscopic aperture 18 formed in metallic film layer 16. First light beam 30 and second light beam 32 may be directly transmitted to pin hole or aperture 18, or may be focused on the pin hole or aperture 18 by a focusing means, such as focusing lens 36. Light beams 30, 32 each have a unique and differing wavelength.

Although first light beam 30 and second light beam 32 may have a wide range of wavelengths, in the preferred embodiment, first light source 26 produces a light beam 30 having a wavelength approximating 632 nm. Further, second light source 28 preferably generates a second light beam 32 having a wavelength approximating 488 nm. These wavelengths are chosen from experimental tests of a wide range of different light sources. In the preferred embodiment, first light source 26 is a He—Ne laser and second light source 28 is an Ar ion laser.

Second light source 28 is selectively operated to selectively prevent tunneling of the photons of beam 30 through the aperture 18. Second light source 28 may be selectively actuated through standard switching means, or may use a separate modulation means 38, such as an optical chopper or other standard means of optical modulation.

Figure 2:
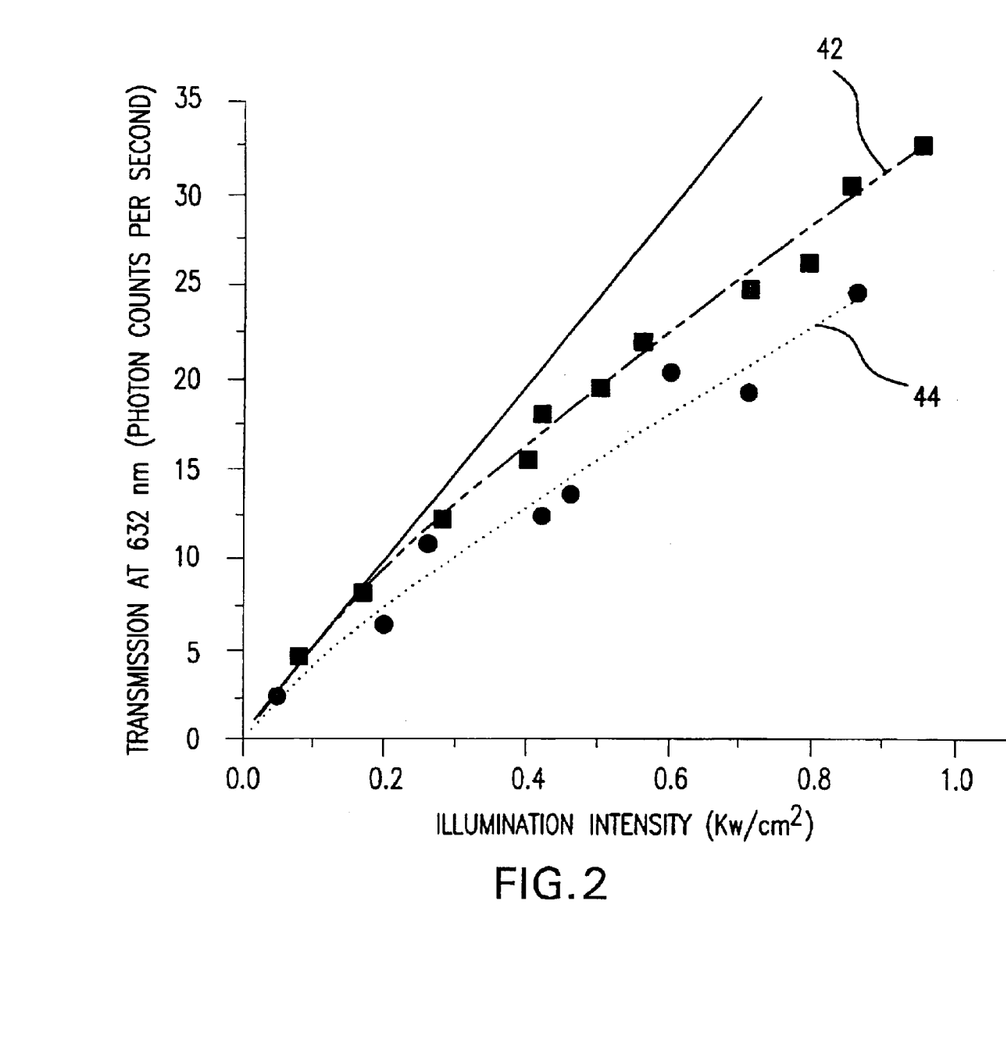
FIG. 2 is a graph comparing the intensity of photon tunneling when only the first light source is actuated and both light sources are also actuated.

FIG. 2 illustrates the transmission of first light beam 30 through aperture 18 both with the light beam 32 also being directed on aperture 18 and without the light beam 32. In FIG. 2, the solid line 42 illustrates the transmission vs. measured illumination intensity for only first light beam 30. The dotted line 44 illustrates the transmission vs. measured illumination intensity when second light source 28 is actuated. As shown in FIG. 2, the transmission of photons from light beam 30 is lowered when second light source 28 is actuated. Transmission is measured in photon counts per second and illumination intensity is measured in KW/cm$^2$.

The illumination intensity is measured by optical fiber tip 22 which transmits the measured intensity signal via a communication line 34 to a lock-in amplifier 42, as shown in FIG. 1. Lock-in amplifier 42 compares the measured intensity signal with a reference signal, which may be drawn directly from second light source 28, from modulation means 38, or may be pre-set. The comparison between the reference signal and the measured intensity signal allows system 10 to be used as an optical gate or switch.

Figure 3:
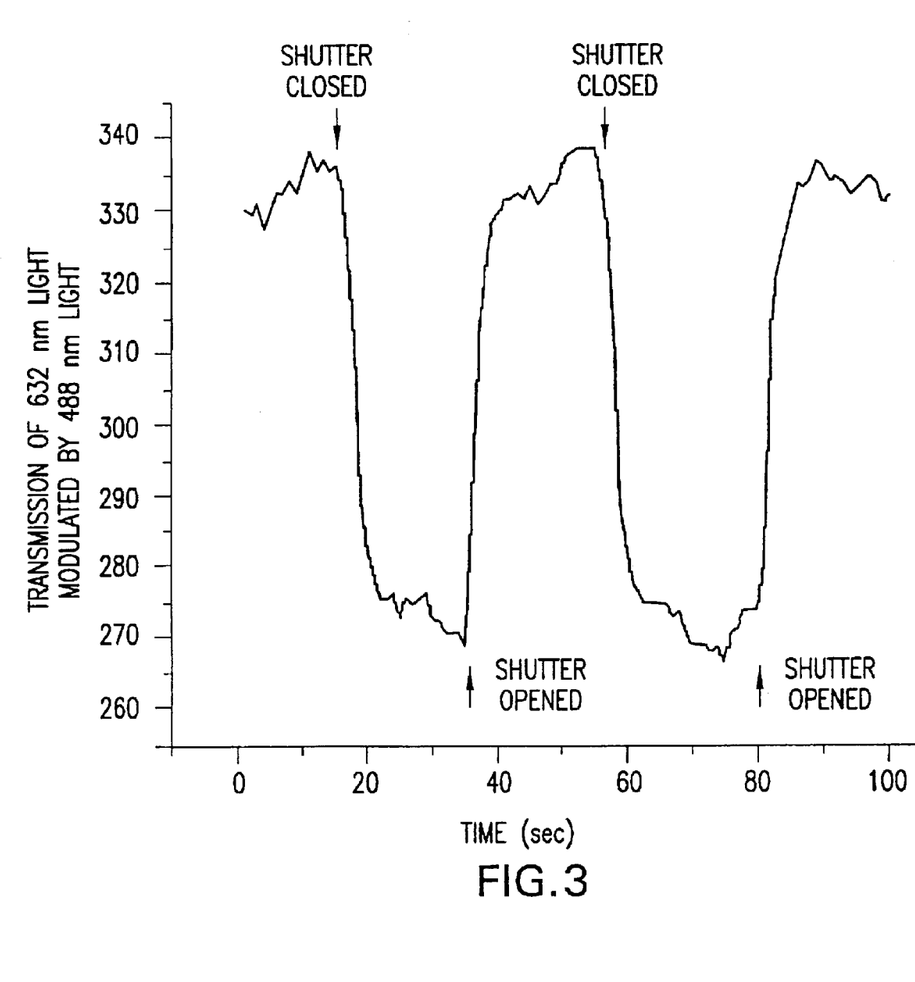
FIG. 3 is a graph illustrating transmission intensity of photon tunneling in the system for optical processing when the second light source is modulated; and, FIG. 4 is a graph illustrating the intensity of light transmission when no non-linear optical film layer is provided in the system.

In order to observe light controlled tunneling directly, second light beam 32 may be modulated by a chopper 38 having a frequency approximating 1.3 kHz. The results of this experiment are shown in FIG. 3 of the Drawings. Light beam 30 transmitted through the pin hole or microscopic aperture 18 is collected by the optical fiber tip 22 and sent to a photomultiplier tube through an optical filter, which completely cuts out the blue light produced by second light source 28. The wavelength-specific filter 40 is illustrated in FIG. 1 coupled to optical fiber tip 22. Modulation of the pin hole transmission at 632 nm induced by modulation of the 488 nm light incident on the same pin hole 18 is observed using lock-in amplifier 42, which uses the chopper sync signal, generated by chopper 38, as a reference. This allows the intensity variations of the 632 nm light tunneling through the pin hole 18 induced by the 488 nm light to be measured directly.

As shown in FIG. 3, a shutter is used to control the first light source 26, which in this experiment is a He—Ne laser, and the shutter is closed and opened twice during the experiment. The signal measured with a closed shutter is taken to be the time-averaged noise of the photomultiplier. As shown in FIG. 3, the gating light induces approximately 15% intensity changes of the signal light. The time behavior of the observed switching is determined by the time constant of the lock-in amplifier, approximately three seconds in this experimental set-up, which is needed for the signal integration. Variation of the chopping frequency between 50 and 2000 Hz is not found to influence the observed modulation depth of the signal light.

Figure 4:
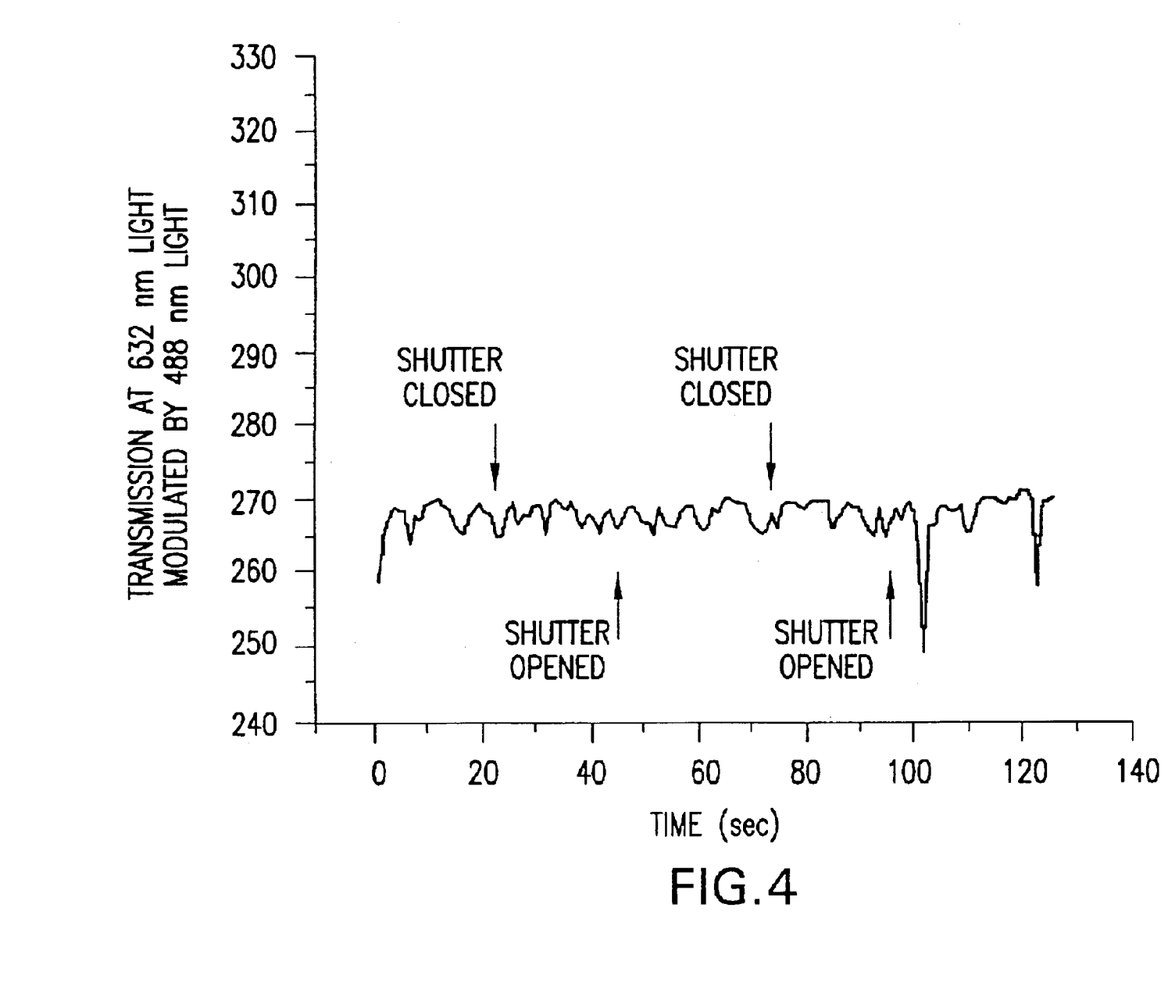

In order to show that the gating effect is related to the non-linear properties of the pin hole 18 covered with the non-linear optical film layer 20, FIG. 4 illustrates the same experiment performed on a similar system, however, the metallic film layer 16 in this set-up does not have a non-linear optical film layer 20 formed thereon. As shown in FIG. 4, no tunneling light modulation was detected in the case without a non-linear optical film layer.

The observed photon blockade effect in the system 10 of FIG. 1 is similar to the Coulomb blockade phenomenon observed in single-electron tunneling experiments. The Coulomb blockade leads to single-electron tunneling in tunnel junctions with an extremely small capacitance, where the charging energy $e^2/2C$ of the capacitance C is much larger than the thermal energy $k_BT$ and the quantum fluctuation energy h/RC, where R is the resistance of the tunnel junction, e is the electron charge and T is temperature.

A single-electron tunnel junction may be formed, for example, by a nanoparticle with a very small capacitance C placed in a gap formed between the tip and sample of a scanning tunneling microscope. In this case, tunneling of a single electron into the nanoparticle results in noticeable charging of the junction capacitance, so the probability of other tunneling events is drastically reduced. Thus, there is a strong correlation between electrons tunneling one at a time and tunneling in steps, known as the so-called "Coulomb Staircase", in the current-voltage characteristic of a tunnel junction.

In an optical single-photon tunneling system, such as system 10 shown in FIG. 1, the system is designed to emulate the geometry of a single-electron tunneling set-up. Classical realization of light tunneling is based on a glass surface illuminated in the total internal reflection geometry; e.g., using a prism, such as prism 12, or a semicylinder. In this case, all incident light is reflected and only an evanescent field (exponentially decaying from the surface) exists over a smooth surface. If a tapered glass fiber, such as the optical fiber tip 22, is placed sufficiently close to the glass-air interface, the evanescent field is transformed into propagating waves in the fiber. Thus, optical tunneling through an air gap (which can be considered as a tunnel barrier) occurs. This geometry is typically used in scanning tunneling optical microscope operation.

Still considering the nanometer-scale object placed within the tunnel gap of the scanning tunneling optical microscope, we assume that the object possesses non-linear optical properties and exhibits well-defined localized electromagnetic modes. In system 10 of FIG. 1, a non-linear layer 20 formed on gold layer 16 is used, however, other materials may be used. Nanometer-size gaps between metal surfaces (such as between a tip, such as optical fiber tip 22, and a sample of a scanning tunneling microscope) are known to exhibit pronounced and well-defined localized surface plasmon resonances. Plasmons are the quanta of waves produced by collective effects of large numbers of electrons in matter when the electrons are disturbed from equilibrium. Metallic materials generally provide the best evidence of plasmons because they have a high density of electrons which are free to move.

The plasmon energy for most metals corresponds to that of an ultraviolet photon. However, for silver, gold, the alkali metals, and a few other materials, the plasmon energy is sufficiently low to correspond to that of a visible or near-ultraviolet photon. This means that there is a possibility of exciting plasmons by light. If plasmons are confined upon a surface, optical effects can be easily observed. In this case, the quanta are called surface plasmons, and they have the bulk plasmon energy as an upper energy limit.

The experimental arrangement employed for optically exciting surface plasmons in a thin film is generally referred to as an attenuated-total-reflection apparatus. This device, which is well-known in the art, is usually a transparent hemisphere of sapphire or quartz with a thin metal film positioned on a base. Light enters through the curved surface and is directed to the base. As the beam is moved so that reflection occurs at ever-smaller angles with respect to the base, the beam reaches the critical angle. Past this angle, the beam is totally reflected internally. Surface plasmon excitation leads to diminished intensity of the reflected light, which is measured at various frequencies.

Excitation of localized surface plasmon modes may lead to very large electromagnetic field intensity enhancement because of the very small volume of these modes. If the frequency of tunneling photons is in resonance with some localized optical mode of the nanometer-scale object, tunneling from the sample into the tip of the scanning tunneling optical microscope is facilitated. This facilitation occurs via excitation of the localized mode. The electric field of the excited localized mode $E_L$ induces local changes in the dielectric constant $\epsilon$ of the non-linear optical material.

When a nanometer-scale non-linear optical object, which exhibits well-defined localized electromagnetic modes, is placed within a tunneling gap, photon tunneling may be facilitated if the frequency of tunneling photons coincides with the frequency of the localized electromagnetic mode. Excitation of such modes may cause local changes in the dielectric constant of the non-linear object given by $$\epsilon = \epsilon_0 + 4\pi \chi^{(3)} |E_L|^2, \qquad (3)$$

where $E_L$ is the local field, and $\epsilon_0$ and $\chi^{(3)}$ are the linear dielectric constant and the third order non-linear susceptibility of the object, respectively. As a consequence of dielectric constant change, the localized modes may experience a noticeable frequency change, so that the tunneling photons will remain out of resonance. Thus, photon tunneling will be blocked in a manner similar to the Coulomb blockade effect for electrons.

The experimental measurements produced by system 10 of FIG. 1, and shown in FIGS. 2 and 3, illustrate that light tunneling through individual sub-wavelength pin holes 18 in a thick gold film layer 18 covered with a layer of 3BCMU polydiacetylene show strong evidence of a photon blockade effect.

Localized surface plasmons of gold nanoparticles, such as those which form gold layer 16, may be understood as cavity modes for propagating surface plasmons. In the limit of large K, where K is the wave number, the spectrum of propagating surface plasmons is defined by $$\epsilon_m = \epsilon_\delta, \qquad (4)$$

where $\epsilon_m$ is the frequency dependent dielectric constant of the chosen metal, and $\epsilon_\delta$ is the dielectric constant of the dielectric around the metal nanoparticle. When using 3BCMU for the non-linear optical film layer 20, $\epsilon_\delta$ is approximately 1.7, so the surface plasmon frequency corresponds roughly to the frequency of 488 nm light in a vacuum, increasing the chances that pin holes 18 will exhibit higher-mode resonances under the excitation with blue light. This is why 488 nm light is preferred for second light beam 32 when gold is used for the metallic film layer 16 and 3BCMU is used for the material of the non-linear optical film layer.

If the geometry of pin hole 18 is modeled as a narrow gap having a width d between two small metal spheres (representing nanometer-sized grains of the polycrystalline film), the non-linear material of film 20 may be assumed to fill the gap. The localized plasmon modes spectrum of such a system can be calculated analytically in the limit of d<<R, since it formally resembles a particle motion in the Coulomb field, and is determined by the dispersion relation $$Re(\epsilon/\epsilon(\omega)) = -(m+\tfrac{1}{2})(d/2R)^{1/2}, m=0,1,2\ldots, \qquad (5)$$

where $\epsilon$ and $\epsilon(\omega)$ are the dielectric constants of non-linear material and metal, respectively, Re is the dispersion, and R is the radius of the sphere. The quantum number m corresponds to different localized surface plasmon modes in the gap. This spectrum suggests considerable differences in the optical properties of the pin holes at different illuminating light wavelengths, which are close or far away from the localized surface plasmon resonance. Thus, different behavior of the pin holes at different wavelengths is expected.

The strongest localization in equation (5) occurs for the lowest, m=0, mode with a localization length given by:

$$L = (2dR)^{1/2}, \qquad (6)$$

and the electric field of this localized mode is determined by the potential:

$$\phi(K) = A \frac{\exp(-kL)}{K\varepsilon}, \qquad (7)$$

where A is the normalization constant.

Having determined the mode volume of this localized plasmon, the respective electric field in the gap can be calculated and the related electro-optical nonlinearity estimated (via equation (3)) for a given number of tunneling photons.

With an increase of the incident light intensity, the LDOS resonance shift leads to significant variations of LDOS at the illumination wavelength. The decrease of the LDOS results in a saturation of transmitted light intensity with an increase of the incident light intensity. Because of very strong field localization, the number of photons required to achieve a "photon blockade" is very low. If $\chi^{(3)}$ is on the order of $10^{-10}$ esu, as assumed, which is on the correct order of magnitude for the $\chi^{(3)}$ observed in 3BCMU and 4BCMU polydiacetylene materials, there is a fair chance to observe single-photon tunneling, since a single tunneled photon causes the reduction of the LDOS at the incident light wavelength by almost a factor of 2.

The experimental data shown in FIGS. 2, 3, and 4 has been fitted assuming the intensity dependent local density of states resonances analogous to the single-electron tunneling/single-photon tunneling model. The localized surface plasmon spectral positions have been used as fitting parameters. Although the absolute spectral positions of the resonances related to nanopores can be somewhat different from those given by the equation for Re, a similar dependence on light intensity has been assumed for fitting.

Unlike the case of a Coulomb blockade, where at $e^2/2C >> k_{BT}$ there is no transmission until a certain voltage is achieved, the experimental curve shown in FIG. 2 exhibits linear growth at small light intensities. The wavelength of light, however, is much larger than the wavelength of electrons, so unlike single-electron tunneling experiments, there is a non-zero probability for photons to nonresonantly tunnel directly into the collecting fiber, such as fiber tip 22 of FIG. 1. On the other hand, the localized plasmon resonances of metal nanoparticles have rather large line width. Thus, the staircase transmission behavior should be much less pronounced compared to the Coulomb Staircase at low temperatures.

Another difference between the Coulomb and photon blockade is due to the fact that unlike electric charge, the number of photons is not conserved. Thus, the dominant decay mechanism of localized plasmons in metallic nanoparticles is nonradiative Landau damping where the electromagnetic energy is transferred to electronic excitations. The "steps" seen in conductance of a Coulomb blockade device are usually of the order of $$\frac{2e^2}{h}.$$

Since the current of photons is not conserved, no similar "universal steps" in experimentally measured photon transmission may be expected.

Utilizing the system 10 of FIG. 1, the photon tunneling of a light beam 30 may be controlled by a light beam 32 having a differing wavelength from that of light beam 30. By selectively actuating light beam 32 for modulating light beam 32 by means of an optical chopper or other modulation means 38, the rate and intensity of photon tunneling of photons from light beam 30 through aperture 18 may be selectively controlled. Thus, system 10 may be used for the creation of optical switching devices, optical gates, and other opto-electronic systems. Low optical throughput of individual pin holes 18 may be compensated by the use of large numbers of pin holes per device area.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described and particular steps may be reversed or interposed, all without departing from the spirit or scope of the invention as defined in the appended claims.

What is claimed is:

1. A system for optical processing based on light-controlled photon tunneling comprising:
    a prism having an upper surface;
    a metallic film layer deposited on said upper surface of said prism, said metallic film layer having at least one microscopic aperture formed therethrough;
    a non-linear optical film layer formed on said metallic film layer and covering said at least one microscopic aperture;
    an optical fiber tip positioned above said at least one microscopic aperture and adjacent said non-linear optical film layer;
    control means for selectively positioning and controlling movement of said optical fiber tip;
    a first light source for generating a first light beam, said first light beam being directed at said microscopic aperture; and,
    a second light source for generating a second light beam, said second light beam being directed at said microscopic aperture, said second light source being selectively actuated to selectively prevent photon tunneling of said first light beam through said microscopic aperture, wherein intensity of transmitted photons is detected by said optical fiber tip.

2. The system for optical processing based on light-controlled photon tunneling as recited in claim 1, wherein said metallic film layer is formed of gold.

3. The system for optical processing based on light-controlled photon tunneling as recited in claim 1, wherein said non-linear optical film layer is formed of a polydiacetylene material.

4. The system for optical processing based on light-controlled photon tunneling as recited in claim 1, wherein said first and second light sources are lasers.

5. The system for optical processing based on light-controlled photon tunneling as recited in claim 1, wherein said first and second light beams each have unique wavelengths.

6. The system for optical processing based on light-controlled photon tunneling as recited in claim 5, wherein said first light beam has a wavelength of 633 nm.

7. The system for optical processing based on light-controlled photon tunneling as recited in claim 6, wherein said second light beam has a wavelength of 488 nm.

8. The system for optical processing based on light-controlled photon tunneling as recited in claim 1, wherein a focusing lens is positioned between first and second light sources and said prism.

9. The system for optical processing based on light-controlled photon tunneling as recited in claim 1, wherein an optical chopper is positioned between said second light source and said prism.

10. The system for optical processing based on light-controlled photon tunneling as recited in claim 9, wherein said optical fiber tip is coupled to a lock-in amplifier for comparison of said intensity of said transmitted photons to a reference signal.

11. The system for optical processing based on light-controlled photon tunneling as recited in claim 1, wherein a wavelength specific filter is coupled to said optical fiber tip.

12. A method for optical processing based on light-controlled photon tunneling comprising the steps of:
    (a) establishing a prism having an upper surface coated with a metallic film layer, said metallic film layer having at least one microscopic aperture formed therethrough, a non-linear optical film layer being formed on said metallic film layer and covering said microscopic aperture;
    (b) projecting a first light beam towards said microscopic aperture;
    (c) projecting a second light beam towards said microscopic aperture; and,
    (d) selectively modulating said second light beam to selectively prevent photon tunneling of said first light beam through said microscopic aperture.

13. The method for optical processing based on light-controlled photon tunneling as recited in claim 12 wherein said step of selectively modulating said second light beam is followed by measurement of intensity of transmitted photons through said microscopic aperture.

14. The method for optical processing based on light-controlled photon tunneling as recited in claim 13 wherein said step of measuring intensity of transmitted photons is followed by comparison of measured intensity to a reference intensity.

15. The method for optical processing based on light-controlled photon tunneling as recited in claim 12 wherein said steps of projecting said first light beam and projecting said second light beam are followed by focusing said first and second light beams on said microscopic aperture.

16. The method for optical processing based on light-controlled photon tunneling as recited in claim 12, wherein said step of selectively modulating said second light beam further includes optical chopping of said second light beam.

17. The method for optical processing based on light-controlled photon tunneling as recited in claim 12, wherein said first and second light beams each have a unique wavelength.

18. The method for optical processing based on light-controlled photon tunneling as recited in claim 17, wherein said first light beam is projected with a wavelength of 632 nm.

19. The method for optical processing based on light-controlled photon tunneling as recited in claim 18, wherein said second light beam is projected with a wavelength of 488 nm.

20. The method for optical processing based on light-controlled photon tunneling as recited in claim 12, wherein said first and second light beams are generated by respective first and second lasers.

21. The method for optical processing based on light-controlled photon tunneling as recited in claim 12, wherein said metallic film layer is formed of gold.

22. The method for optical processing based on light-controlled photon tunneling as recited in claim 12, wherein said non-linear optical film layer is formed of a polydiacetylene material.

* * * * *